United States Patent
Gomez

(10) Patent No.: US 8,142,388 B2
(45) Date of Patent: Mar. 27, 2012

(54) APPARATUS TO FACILITATE REMOVAL OF CATARACTS OF FROM THE EYES

(76) Inventor: Mario P. Gomez, Ladue, MO (US)

( * ) Notice: Subject to any disclaimer, the term of this patent is extended or adjusted under 35 U.S.C. 154(b) by 19 days.

(21) Appl. No.: 12/587,587

(22) Filed: Oct. 9, 2009

(65) Prior Publication Data

US 2010/0036388 A1   Feb. 11, 2010

Related U.S. Application Data

(63) Continuation-in-part of application No. 11/656,869, filed on Jan. 22, 2007, now abandoned.

(60) Provisional application No. 60/855,278, filed on Oct. 30, 2006.

(51) Int. Cl.
 *A61B 17/20* (2006.01)
(52) U.S. Cl. .......................... 604/22; 604/264
(58) Field of Classification Search ............ 604/22, 604/272, 264, 275, 294; 606/107, 167, 169
 See application file for complete search history.

(56) References Cited

U.S. PATENT DOCUMENTS

| | | | |
|---|---|---|---|
| 3,990,452 A | 11/1976 | Murry et al. | |
| 4,989,583 A * | 2/1991 | Hood | 601/2 |
| 2004/0152990 A1 | 8/2004 | Mackool | |
| 2004/0153026 A1 | 8/2004 | Mackool | |
| 2004/0158236 A1 | 8/2004 | Thyzel | |
| 2004/0167504 A1 | 8/2004 | Thyzel | |
| 2004/0193104 A1 | 9/2004 | Jervis | |
| 2004/1093121 | 9/2004 | Kadziauskas et al. | |
| 2004/0199171 A1 | 10/2004 | Akahoshi | |
| 2004/0199192 A1 | 10/2004 | Akahoshi | |
| 2004/0267211 A1 | 12/2004 | Akahoshi | |
| 2005/0020990 A1 | 1/2005 | Akahoshi | |
| 2005/0043671 A1 | 2/2005 | Rockley et al. | |
| 2005/0054971 A1 | 3/2005 | Steen et al. | |
| 2005/0059939 A1 | 3/2005 | Perkins et al. | |
| 2005/0096680 A1 | 5/2005 | Zacharias | |
| 2005/0113741 A1 | 5/2005 | Huang et al. | |
| 2005/0154409 A1 | 7/2005 | Mackool | |
| 2005/0209621 A1 | 9/2005 | Gordon et al. | |
| 2005/0228423 A1 | 10/2005 | Khasayar et al. | |
| 2005/0228424 A1 | 10/2005 | Khasayar et al. | |
| 2005/0228425 A1 | 10/2005 | Boukhny et al. | |
| 2005/0244478 A1 | 11/2005 | Hughes et al. | |
| 2005/0244479 A1 | 11/2005 | Huang et al. | |
| 2005/0244500 A1 | 11/2005 | Whitcup et al. | |
| 2005/0244506 A1 | 11/2005 | Burke et al. | |
| 2005/0244512 A1 | 11/2005 | Holekamp et al. | |
| 2005/0244845 A1 | 11/2005 | Ruben et al. | |

(Continued)

*Primary Examiner* — Jackie Ho
*Assistant Examiner* — Laura Schell
(74) *Attorney, Agent, or Firm* — Paul M Denk

(57) ABSTRACT

This apparatus is a device for removal of cataracts from the eyes of patient. The apparatus includes a hand piece, with an irrigation water line, a vacuum line and a power line provided therein, are all connected with the hand piece. Within the hand piece the vacuum line is attached to a tube, identified as the horn, concentric with the outer shell of the hand piece. Through a hooks and slider joint, bayonet type or threaded joint in the front end, the horn connects with a surgical needle. At the front end of the irrigation tube it discharges water into a chamber, which irrigation water passes between the needle and an outer sleeve and into the anterior chamber of the eye. Ultrasonic waves transmitted to the horn are conveyed to the tip of the needle where the axial vibrations of the tip may be used to comminute cataract material.

3 Claims, 6 Drawing Sheets

U.S. PATENT DOCUMENTS

| | | |
|---|---|---|
| 2005/0245497 A1 | 11/2005 | Penfold et al. |
| 2005/0245910 A1 | 11/2005 | Wright et al. |
| 2005/0249735 A1 | 11/2005 | Lee et al. |
| 2005/0249775 A1 | 11/2005 | Falotico et al. |
| 2005/0249776 A1 | 11/2005 | Chen et al. |
| 2005/0251105 A1 | 11/2005 | Peyman |
| 2005/0251253 A1 | 11/2005 | Gross |
| 2005/0251254 A1 | 11/2005 | Brady et al. |
| 2005/0256076 A1 | 11/2005 | Bumcrot |
| 2005/0256081 A1 | 11/2005 | Peyman |
| 2005/0260161 A1 | 11/2005 | Alitalo et al. |
| 2005/0260180 A1 | 11/2005 | Wei et al. |
| 2005/0260186 A1 | 11/2005 | Bookbinder et al. |
| 2005/0261628 A1 | 11/2005 | Boukhny et al. |
| 2005/0261715 A1 | 11/2005 | Boukhny et al. |
| 2005/0267504 A1 | 12/2005 | Boukhny et al. |
| 2006/0047241 A1 | 3/2006 | Boukhny |
| 2006/0047254 A1 | 3/2006 | Akahoshi |
| 2006/0084961 A1 | 4/2006 | Kadziauskas et al. |
| 2006/0135975 A1 | 6/2006 | Perkins |
| 2006/0135976 A1 | 6/2006 | Perkins |
| 2008/0114313 A1* | 5/2008 | Gomez et al. .................. 604/294 |

* cited by examiner

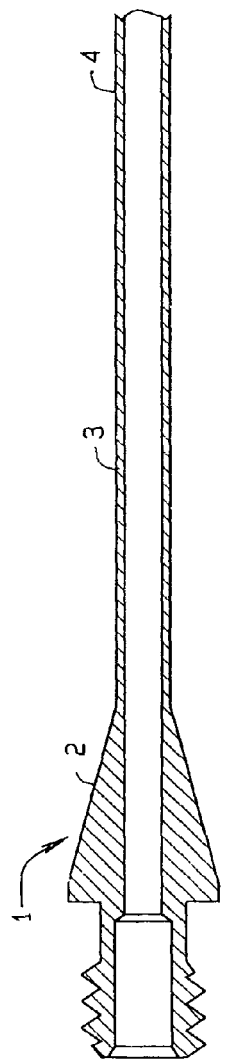
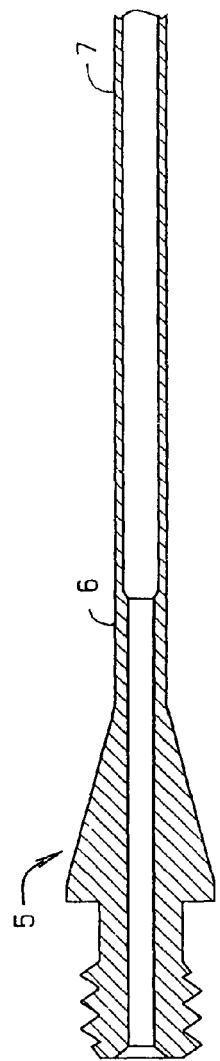
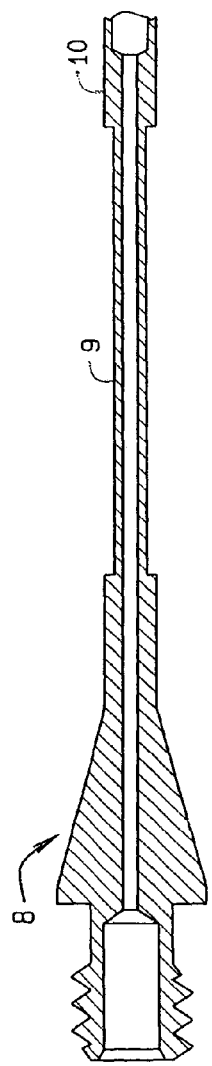
FIG. 1A
FIG. 1B
FIG. 1C
PRIOR ART

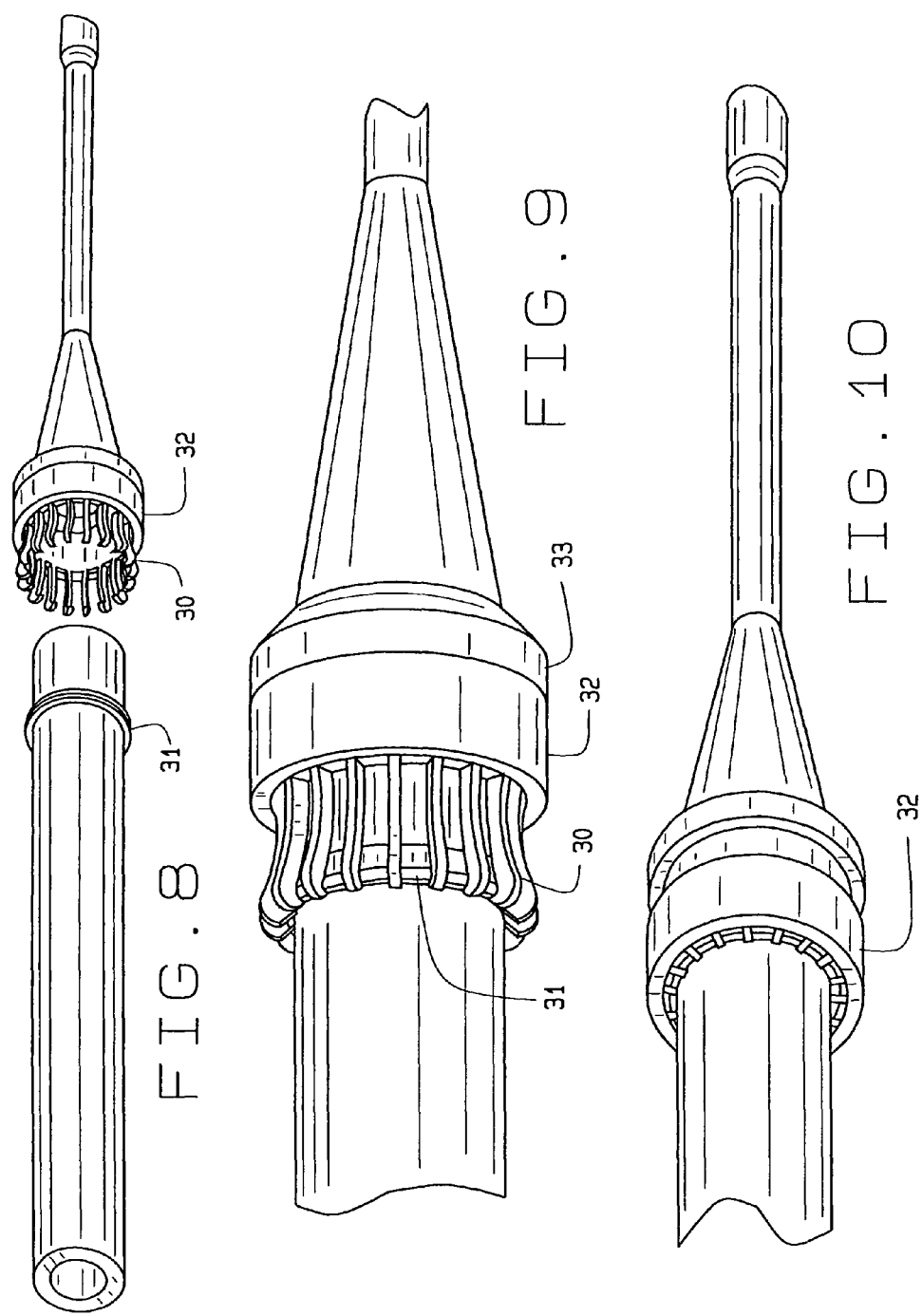

APPARATUS TO FACILITATE REMOVAL OF CATARACTS OF FROM THE EYES

CROSS-REFERENCE TO RELATED APPLICATION

This continuation-in-part application for patent claims priority to the non-provisional patent application having Ser. No. 11/656,869, which was filed Jan. 22, 2007, now abandoned, which claims priority to the provisional patent application having Ser. No. 60/855,278, which was filed on Oct. 30, 2006.

BACKGROUND OF THE INVENTION

This invention relates to a needle-horn configuration which significantly reduces the heat generated in the needle. Available needles may become hot enough to damage the cornea tissue on the incision through which the needle penetrates into the anterior chamber of the eye.

To date there is a significant number of needles with different characteristics. A careful analysis of their similarities and differences would show that their effect on the needle performances is minimal. Some have smooth surfaces and some striated surfaces. Some have left handed threads and others have right handed threads. To minimize the size of the incision some needles have smaller diameters than others. The configurations of the tips themselves may also vary from needle to needle, but none of the available needles have tips which are hydrodynamically significantly better than the others. In other words, their suction power is roughly the same and relatively low.

All needles analyzed to date use the same type of attachment: horn with internal thread and needle with external thread. It is the main, and extremely important, technical advantage of our invention that we exchange the positions of the threads in the horn and in the needle. In one of the embodiments the needle has the internal thread while the horn has the external thread. With this arrangement the ultrasound waves may travel in an almost continuous and uniform path from the transducer to the tip of the needle. Furthermore, our design includes an element that it is not used by any other needle. Presently available needles establish direct contact between the horn's vertical front end surface and the mating vertical surface of the needle hub. Both the horn and the needle are made of titanium alloy (Ti-6Al-4V) in a relatively hard condition. It would be technically impossible that both surfaces were perfectly planar and parallel using the technology used at present. The areas of contact would be a small percent of the total area. The ultrasound waves would be reflected back by the contact free areas of the horn. Because of the needle hub geometries in use today, even those waves that cross the areas of contact would be subjected to multiple reflections within the hub with the consequent generation of significant amounts of heat and increasing temperatures in the hub and needle.

The problems described in the previous paragraph are eliminated in our invention. The interface problem is eliminated by placing a 0.005" thick washer of annealed and magnetized pure nickel. Such a washer could be in a range of about 0.002" to 0.050" in thickness. The washer has the same internal diameter as both the horn and the needle. The outside diameter of the washer is equal to the outside diameter of the horn front surface. When the needle and the horn are tightened together the applied torque will generate enough pressure on the washer that it will deform completely filling the space between the end surfaces of the horn and the needle hub. Two positive effects will take place due to the tightening of the needle-horn joint. The gaps resulting from the machining irregularities will be eliminated and, because Ni has an ultrasound speed very close to that of Ti-6Al-4V, a large percentage of the arriving waves will go through the interface with minimum losses and great reduction in heat generation.

SUMMARY OF THE INVENTION

This invention addresses three operational needs resulting from the inadequate design of all present surgical needles used in the removal of cataracts. The attachment of the needle to the horn created a tortuous path for the ultrasonic waves to travel from the transducer to the tip of the needle. Furthermore, the interface between the horn front end and the mating face at the needle hub resulted in a very inefficient transmission of waves from the horn to the needle. Lastly, the designs of the tips of the needles are so simple minded and inefficient that the removal of cataract debris is difficult, resulting in longer operating times than necessary.

The inefficient transmission of the ultrasonic waves also has a tendency to cause a build up of energy that generates heat in the needle, at its juncture with the horn, which can cause a hazard to the ophthalmologist and other technicians handling of this apparatus during usage, and actually interfere with their efficient performance during a cataract operation.

To address the previously described shortcomings three main improvements were added to this invention: 1) In the basic embodiment referred to as "threadlock needle", the threaded ends of the horn and the needle were exchanged in comparison with presently used surgical needles, as shown in FIG. 1; the external threads of the joint are now in the front end of the horn while the internal thread is on the rear end of the needle. As a result the ultrasonic wave path is free of heat promoting interferences. 2) In the "twistlock" preferred embodiment the threaded joint is replaced entirely by a bayonet type joint that completely eliminates all barriers to the advance of the ultrasonic waves. 3) In a second preferred embodiment the threaded joint is replaced entirely by a different approach where the horn is, basically, a smooth hollow cylinder with a built in retaining ring locked to the needle by a group of hooks actuated by a sliding ring. The front end of the horn is pressed against the Ni washer and the matching surface on the rear of the needle. 4) The addition of a magnetized and annealed Ni washer at the interface between the horn front face and the needle back face will allow the transmission of a much higher percent of the ultrasound waves than is possible with present needles and horns. The sound speed in Ti and Ni (magnetized) are very close: 6070 m/s and 6040 m/s respectively. 5) The use of a Venturi nozzle at the tip of the needle will increase the dragging force of the suction water at the tip of the needle by as much as a factor of twenty.

It is, therefore, the principal object of this invention, to provide a path to the ultrasound waves such that they can travel from the transducer to the tip of the needle with minimum energy dissipation.

Another object of this invention is to reduce the heating of the needle below temperatures which may otherwise damage cornea tissue.

A further object of this invention is to reduce the ultrasound power required to operate the needle without overheating but without losing the attrition power of the needle tip.

Another object of this invention is to incorporate at the tip of the needle a Venturi type nozzle to increase substantially the suction power of the needle tip.

Still another object of this invention is to, eventually, replace the present silicon elastomer irrigation sleeve with a Ti one.

Another object of this invention is to incorporate in the fabrication of the needles methods such as "diffusion bonding" and "super-plastic forming" widely used in the aero space vehicle fabrication using Ti, and Ti alloys, with more flexibility and control than those methods used today to fabricate the needles.

Other objects of this invention may become more apparent to those skilled in the art upon review of the Summary of the Invention as provided herein, and upon undertaking a study of the description of its preferred embodiments, in view of the drawings.

The invention relates to devices that are used to remove cataracts from the eyes of patients. These devices are designed in such a fashion that several, and different, functions are, typically, integrated within the body of a single hand-piece. On the back end of the hand-piece the irrigation water line, the vacuum suction line and the power line, are connected to the hand-piece. Within the hand-piece the vacuum line is attached to a tube, called the "horn", concentric with the outer shell of the hand-piece and connected, as in our first embodiment, through a threaded joint in the front end, to a surgical needle. The irrigation line is connected, in some embodiments, on the back side of the hand-piece to a rigid tube which follows the external contour of the hand-piece. In the front end the irrigation tube discharges the water into a chamber which, itself, discharges the irrigation water into an annular space defined by the surgical needle on the inside boundary and an a molded elastomer or metallic sleeve on the outside boundary. The back end of the sleeve is attached to a coupling integral with the front end of the hand-piece; the front end of the sleeve rests tightly around the tip of the needle. One or more holes are placed towards the end of the sleeve so the irrigation water may be delivered into the anterior chamber of the eye close to the needle tip but in a direction away from the tip. As already mentioned, the vacuum line is attached to the rear end of the horn thereby allowing the water and cataract fragments in the anterior chamber of the eye to be suctioned away from the chamber. To improve the suction power of the needle the tip will take the shape of a Venturi nozzle. The heart of the whole system is the needle, which in its original design (designated "threadlock needle") is attached to the forward end of the horn through an external thread in the horn and an internal thread in the needle. Alternatively, in the first preferred embodiment (designated "twistlock needle") the threaded joint is replaced by a bayonet type joint and, in the second preferred embodiment (designated "slidelock needle") the joint is made up of a set of hooks actuated by a sliding ring that pushes the hooks inwards towards the locking ring in the horn; thereby preventing the separation of the needle from the horn and, simultaneously, exerting a very strong force on the washer and the needle. Finally, the power line carries high frequency electrical signals to an ultrasonic transducer concentric and in contact with the horn. The ultrasonic waves transmitted to the horn are conveyed to the tip of the needle where the axial vibrations of the tip may be used to comminute cataract material. In summary, the complete system consists of these few elements and functions: an irrigation tube that controls the supply of water to the needle/sleeve system, a flexible sleeve that carries the irrigation water to the anterior chamber of the eye through holes on the tip of the sleeve, an anterior chamber between the cornea and the crystalline lens, and a posterior chamber between the iris and the lens. The tip of the needle suctions the liquid in the anterior chamber as a result of the vacuum applied on the back end of the hand-piece and transmitted through the inner tube of the horn. Also, and very critical, is the transmission of ultrasound waves (US waves) from the transducer to the tip of the needle. All present needle designs, under certain power and cycle conditions, generate a great deal of heat due to the inadequate design of the ultrasound wave path. By having the horn end with an internal thread and the needle with a matching external thread the sound waves are forced to follow a tortuous path with multiple reflections and, consequently, large generation of heat. In some instances cornea tissue in contact with the needle has been damaged by said heat. Our patent, in particular in a possible embodiment, is based on providing a smooth path for the ultrasound waves by having the external thread on the horn and the internal one on the needle. In two preferred embodiments of this patent the threads are either replaced by a bayonet type joint (twistlock) or by an array of hooks actuated by a sliding ring (slidelock), that completely eliminates any possible barriers to the US waves but for the unavoidable direct contact between the horn/washer/needle hub interfaces. The latter should pose only a minor perturbation.

BRIEF DESCRIPTION OF THE DRAWINGS

In referring to the drawings, FIGS. 1A-C show three variations upon prior art needle-horn configurations;

FIG. 8 shows the slidelock embodiment with the locking slider in the retracted position and the hooks in the open position;

FIG. 9 shows the slidelock embodiment with the locking slider in the operational position and the hooks attached to the horn ring;

FIG. 10 shows the slidelock embodiment locked into position holding the needle to the horn;

DESCRIPTION OF THE PREFERRED EMBODIMENTS

In reference to the drawings, and in particular FIGS. 3, 4, 5, 6, 7, 8 and 9 the preferred embodiments are shown. In these preferred embodiments the complete elimination of barriers to the advance of ultrasonic waves has been achieved.

The foreseeable success of the preferred embodiments is due to a remarkable simplification of its design resulting in almost complete elimination of all spurious interferences to the advance of the ultrasonic waves from transducer to nozzle.

Figure 4:
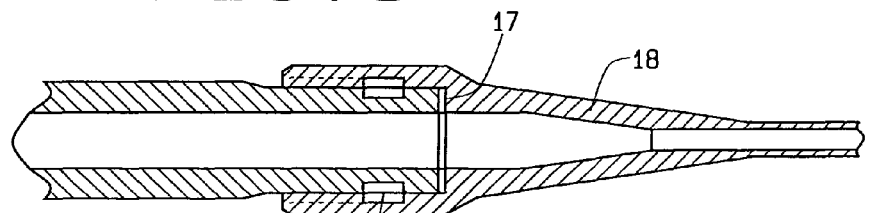
FIG. 4 discloses a modified embodiment of the apparatus with a twistlock device to attach the horn to the needle.
Figure 5:
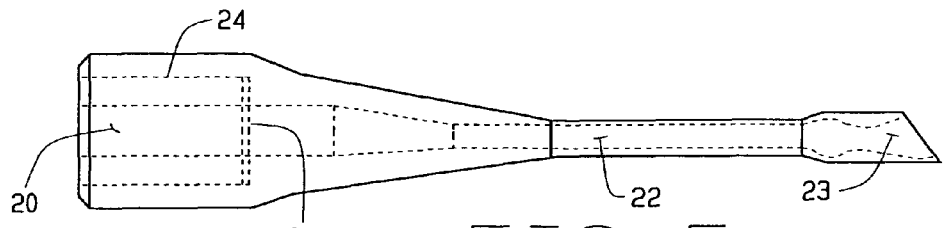
FIG. 5 provides a partial view of the horn and needle apparatus with a twistlock or bayonet mechanism for locking the two together.
Figure 6:
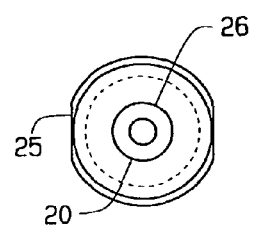
FIG. 6 is a back view of the needle as shown in FIG. 5 and including torqueing flats.

In the twistlock embodiment shown in FIGS. 4, 5 and 6, the locking pins in the horn are press fitted to the horn and made of the same alloy as the horn and the needle, hence, they cannot pose any problem to the advance of the ultrasonic waves.

Figure 7:
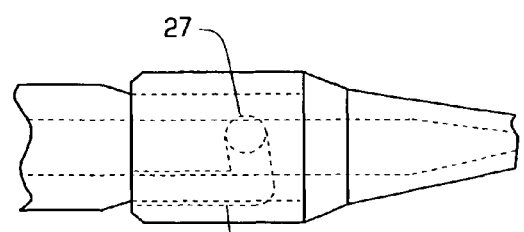
FIG. 7 shows the interconnection between the horn and the neede is a bayonet type of lock, as noted at 27 and 28.

In the slidelock embodiment shown in FIG. 7 the hooks are in the open position and the sliding ring is pressed forward against the hub flange. See also FIG. 8. In FIG. 9 the slider ring is shown in contact with the stops on the tips of the hooks while themselves are pressed by the ring against the edge of the horn ring producing a significant force between the horn, the washer and the needle.

The path of the ultrasonic waves from transducer to needle tip is now free of obstacles. Furthermore, compared with the nozzles of all previous needles, the Venturi can produce suction forces in an order of magnitude higher than those obtained with the simple apertures used at the tips of all previous needles.

Summarizing, the preferred embodiments of this invention have been simplified to an extreme such that:

a) The sources of uncontrolled heat have been completely eliminated by providing for the ultrasonic waves a path free of any obstacles from the transducer to the tip of the needle.

b) The geometry of the needle has been greatly streamlined, hence, the flow of ultrasonic waves and suction water will not be hindered by obstacles that may result in losses due to heat generation and/or cavitation.

c) The attachment of the needle to the horn has been simplified in its operation and fabrication.

d) From the medical point of view some advantages are evident:

The superior suction ability of this invention will make it easier to remove cataract debris.

The durations of the operations can, therefore, be shortened.

The danger of cornea damage can be completely suppressed.

FIGS. 1A-C show three variations of needles which are in use today. They do not differ much from each other. Needle 1A exhibits a relatively large suction tube without any attempt to implement some kind of nozzle. Needle 1B exhibits also a large diameter suction tube but half way to the threaded end introduces a sudden restriction with an exit hole which produces a significant amount of turbulence without increasing the suction power at the tip entrance, where higher suction is necessary. Finally, Needle 1C is widely used based on the assumption that the longitudinal striations improve the passage of the irrigation water between the sleeve and the metal tube. In practice, this needle does not perform any better than the others, it costs more to produce and requires a longer incision in the cornea.

Figure 2:
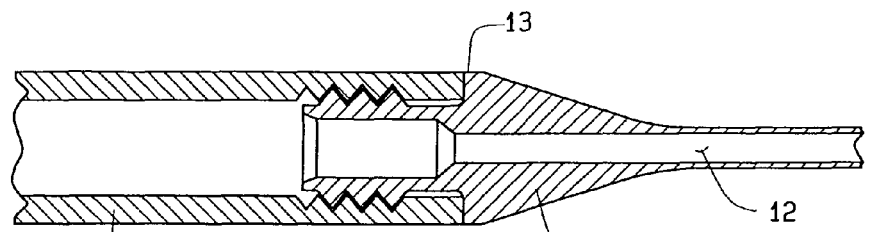
FIG. 2 shows prior art attachment between the horn and needle as currently used by the professionals.

FIG. 2 shows the means of attachment between the horn 11 and the needle 12 that is used by the great majority, if not all, of the brands and eye surgeons. When the ultrasonic waves, at velocities over 500 m/s, reach the threaded joint they are subjected to multiple reflections at the threads, at the contact surface 13 between horn and needle hub, and, also, inside the hub 1 of the needle where they are reflected at the walls of the hub, and interfered by other strayed waves.

Figure 11:
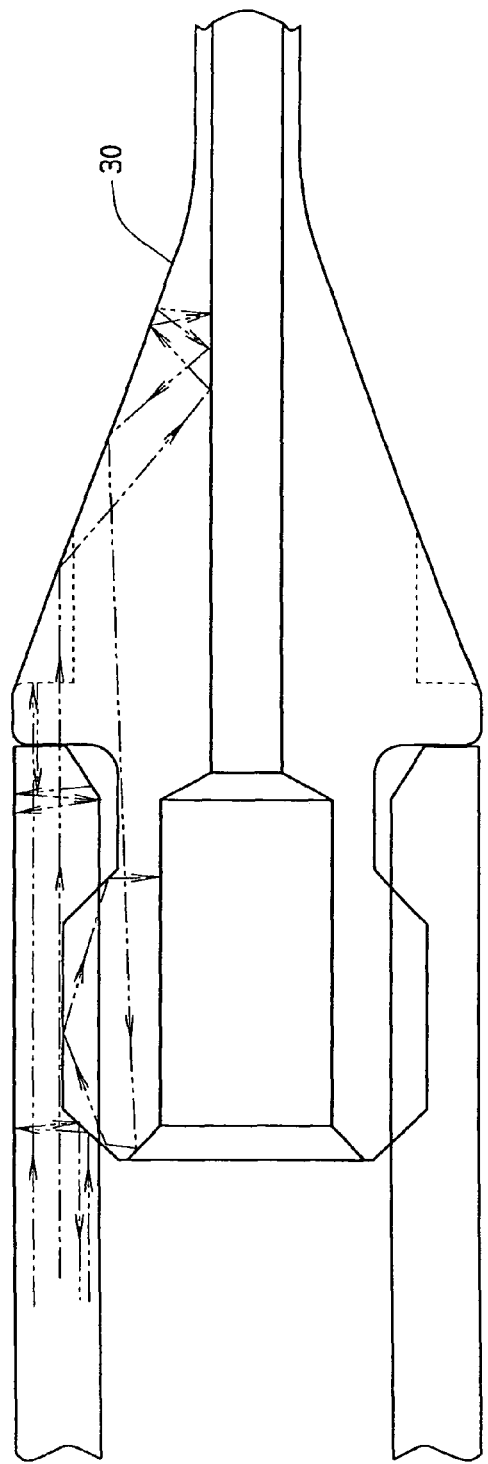
FIG. 11 discloses the interference caused in the transmission of the ultrasonic waves from the horn and into the needle when the prior art and standard type of interconnection is formed having air gaps between these components, and which wave interference and its congestion, as noted, generates a significant amount of heat at this juncture.

As can be seen in FIG. 11, where the horn thread engages onto the back end of the needle, and abuts against the shoulder of the needle, the transmission of the ultrasonic waves through the horn, and into the needle, becomes obstructed, because of the abutting surfaces provided, causing the ultrasonic waves to congest at the smaller tapered section of the needle as noted, where heat of significant proportions can be generated to the detriment of usage of this particular prior art apparatus. It has been determined that as many as seventy percent of the generated ultrasonic waves, being transmitted, can be reflected back, which causes that shown congestion and the generation of heat within the prior art style of needle.

Figure 3:
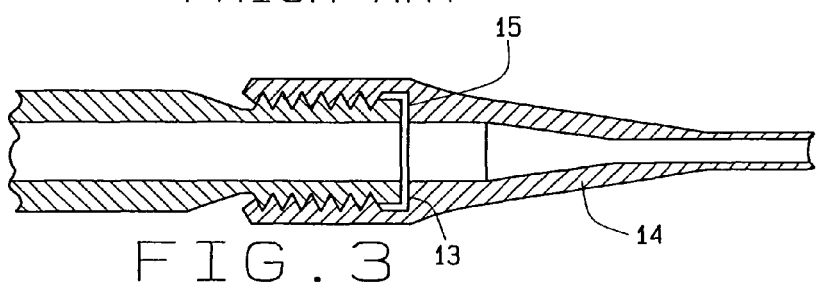
FIG. 3 shows an embodiment of the current invention with a threadlock device where external threads on the front of the horn and the internal threads provided on the hub furnish interconnection between the two with minimum interference.

FIG. 3 shows an embodiment of this invention where the external thread is machined on the front end of the horn and the internal thread is machined in the hub of the needle. One can easily see that the waves coming in the horn from the left could continue through the interface 15, washer 13, threads 16 and modified hub 14 to the tip of the needle with a minimum of interference from the threads.

FIG. 4 shows a second and preferred embodiment of the approach shown in FIG. 3. In this case the thread is completely eliminated and replace by a bayonet type, twistlock engagement 19, washer 17, and hub 18. This embodiment represent just about the optimum solution to the problem of perturbations to the motions of the ultrasonic waves.

FIG. 5 shows more complete details of the twistlock style of lock, as at 19, with the suction tube 20 provided within the needle, and the rear end of the needle including the identified Ni washer 17. Reference 22 shows the needle itself, with the suction tube extending therethrough, and 23 discloses a uniquely shaped Venturi, at the front nozzle, effectively increasing the dragging force of the water at the tip of the needle, to enhance its operations. Reference 24 shows the smooth end of the horn, and inserted within the bore of the needle and 21 shows the grooves of the bayonet type locking.

FIG. 6 shows a backside view of the complete needle where the torqueing flats on the hub 25 and the internal diameters of the suction tube in the horn and part of the hub flange 20 and in the needle itself 22 and the Venturi 23 as shown in FIG. 5. The smallest diameter of the Venturi 23 is equal to that of the needle hub 22.

FIGS. 5 and 6 show the embodiment of what can be considered the optimal design of a surgical needle for the removal of cataracts. The virtues of this embodiment of this invention consists in the elimination of problems that plague other designs: uncontrolled heating even at lower ultrasonic power settings, elimination of potential incompatibility between horn and needle by the addition of Ni washer between them and a Venturi type nozzle at the tip. The interface of the needle with the horn consists of two parts. See FIG. 5. A cylindrical part 24 and a front part 17 that includes the Ni washer. The suction tube 20 consists of four segments, including the Venturi nozzle 23, with smooth transition between them guaranteeing the elimination of cavitation, and concomitant pressure losses. In particular FIG. 5 shows a more detailed sketch of the proposed mechanism to lock the horn and needle hub together, 19 is the locking pin in the horn and 21 is the guiding groove in the hub. This mechanism will eliminate all geometrical interferences, except for the washer, to the advance of the ultrasonic waves from the transducer to the tip of the Venturi.

FIGS. 8-10 show details of the mechanism involved in the slidelock joint design. The joint incorporates the use of flexible hooks 27 to attach the needle to the horn. The latter has an integral attachment ring 28 which is an integral part of it. The operation required to engage or disengage the hooks 27 is performed by a sliding ring 29, on the periphery. When the ring is in contact with the hub flange 33 the hooks are disengaged with the horn. When the ring is slid to the opposite end, the hooks engage the horn ring 28 and press the horn against the washer and the needle.

Figure 12:
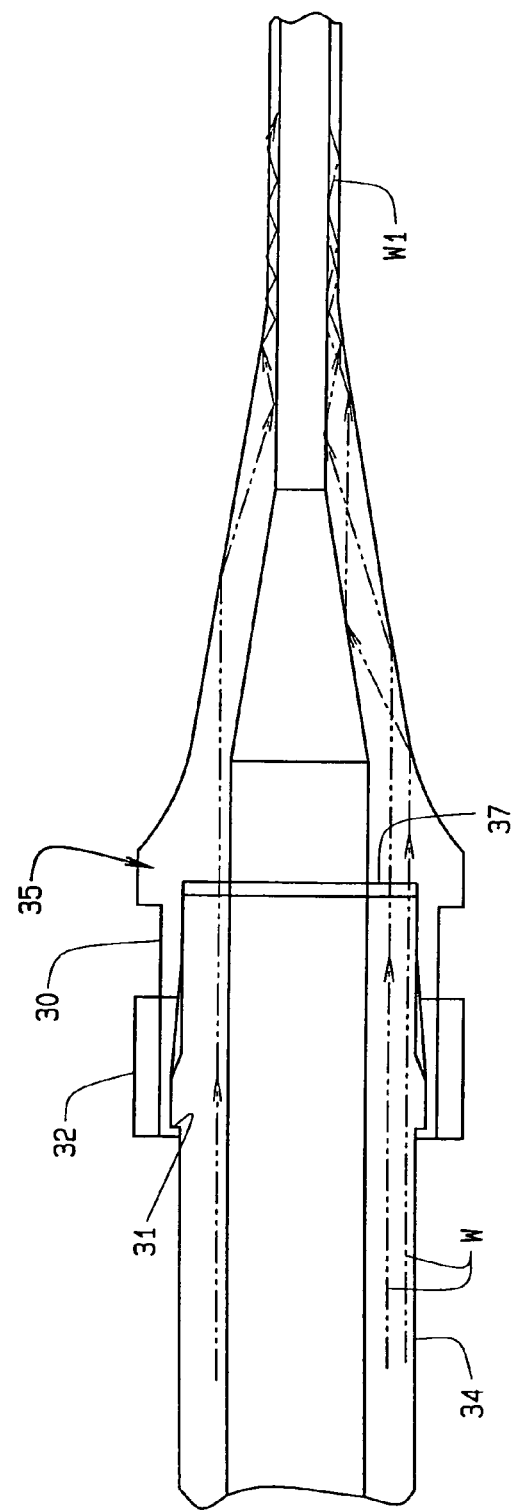
FIG. 12 shows how the current invention routinely passes the ultrasonic waves from the horn and into the needle and forwardly thereof to its tip for use in the effective fracture of cataracts during an operation, all without the generation of any noticeable heat.

As can be seen in FIG. 12, the advantages of providing a hub that engages or interlocks within the back end of the needle can be readily seen. As noted, the horn end 31 engages internally within the back end of the needle, as can be seen at 30. In this particular embodiment, the integral attachment ring 32 cooperates with the sliding ring 31, to hold the various hooks 30 in place. The Ni washer 37 locates between the front of the horn, and the internal back end of the needle, as at 32, to provide a very compatible fit between the two components. Thus, when ultrasonic waves are transmitted through the horn, as noted at w, they are transmitted directly through the washer and into the needle, and encounter little or no obstruction to their continuing flow, as noted at w1, towards the front of the needle, where the ultrasonic waves fracture the cataracts for their removal during this operation.

Figure 13:
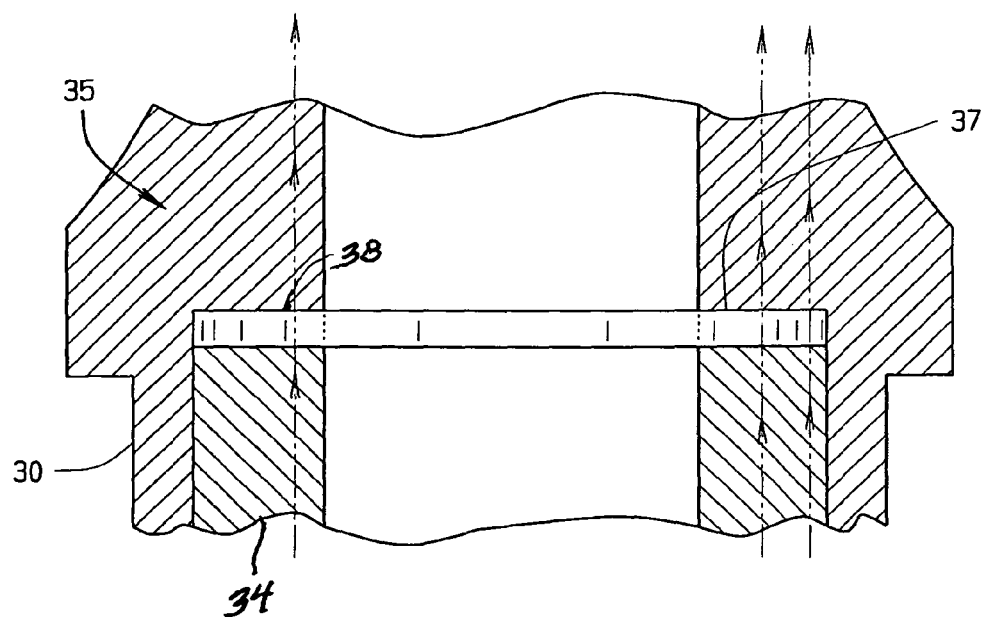
FIG. 13 shows the location of the nickel washer which occupies all space between the front of the horn, and the interior back shoulder of the hub.

As can be seen in FIG. 13, the Ni washer 37 occupies all space between the internal shoulder, as at 38, of the needle 35, and the washer occupies all space, leaving no air gaps at its interface with the internally threaded horn 34. Thus, as can be noted, the ultrasonic waves pass directly from the horn into the needle and are not disrupted as a result of the presence of any air gaps, such as occurs in the prior art style of apparatus as shown in the prior art, and as identified and described in FIG. 11.

Variations or modifications to the subject matter of this invention may occur to those skilled in the art upon review of the development as provided herein. If within the scope of this development, are intended to be encompassed within the invention as described. The depiction of the preferred embodiments, and their disclosure in the drawings, are set forth for illustrative purposes only.

I claim:

1. An apparatus to facilitate removal of cataracts from the eyes, said apparatus including a hand piece for grasping by the physician during performance of a cataract operation, said hand piece including a horn to convey ultrasonic waves generated by the transducer to the back end of a needle, said needle interconnected with the front end of the horn, the needle being applicable for transmission of ultrasonic waves to the cataract, and to provide for a very high frequency alternating force at the needle tip to fracture the cataracts, the front end of the horn having external threads to facilitate its joining with the back end of the needle, and the back end of the needle having internal threads to provide for their threaded engagement onto the horn threads, and an annealed nickel washer provided at the interface between the front end of the horn and the back end of the needle, said nickel washer provided for eliminating any gaps between the front end of said horn and the back end of said needle, and to occupy all space without any air gaps at the interface thereof, the front end of the horn having a front face, the back end of the needle having a back face, and said nickel washer being located and compressed intermediate thereof to facilitate and enhance the uniform flow of the ultrasonic waves therethrough without any significant temperature increase and uncontrolled heating for the apparatus needle, and through such threaded connection providing for the transmission of a higher percentage of ultrasonic waves through the needle and to the cataracts for fracture and removal; said apparatus including a venturi nozzle at the tip of the needle, to increase a vacuuming force of the suction water at the tip of the needle to facilitate the vacuum removal of the pieces of fractured cataract from the eyes anterior chamber during the performance of an operation.

2. The apparatus of claim 1 and wherein the front end of the horn includes a front face, the back end of the needle includes a back face, and said nickel washer being magnetized and annealed, and compressed between the two said faces for enhancing the transmission of ultrasonic waves through the apparatus during its usage.

3. The apparatus of claim 2 and wherein the front end of the horn includes a front face, the back end of the needle includes a back face, and said magnetized nickel washer compressed between the two said faces to enhance the transmission of ultrasonic waves through the apparatus during its usage.

* * * * *